US008988515B2

(12) United States Patent
Takahashi et al.

(10) Patent No.: US 8,988,515 B2
(45) Date of Patent: Mar. 24, 2015

(54) ENDOSCOPE SYSTEM

(71) Applicant: Olympus Medical Systems Corp., Tokyo (JP)

(72) Inventors: Hidetsugu Takahashi, Hachioji (JP); Ryohei Kagawa, Hachioji (JP); Manabu Ishizeki, Hachioji (JP); Hidenori Hashimoto, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 2 days.

(21) Appl. No.: 13/735,182

(22) Filed: Jan. 7, 2013

(65) Prior Publication Data

US 2013/0176410 A1  Jul. 11, 2013

Related U.S. Application Data

(63) Continuation of application No. PCT/JP2012/066899, filed on Jul. 2, 2012.

(30) Foreign Application Priority Data

Jul. 5, 2011  (JP) ................. 2011-149463

(51) Int. Cl.
 *A62B 1/04*  (2006.01)
 *A61B 1/04*  (2006.01)
 (Continued)

(52) U.S. Cl.
 CPC ............. *A61B 1/00009* (2013.01); *A61B 1/045* (2013.01); *A61B 1/05* (2013.01); *H04N 5/357* (2013.01); *H04N 2005/2255* (2013.01);
 (Continued)

(58) Field of Classification Search
 None
 See application file for complete search history.

(56) References Cited

U.S. PATENT DOCUMENTS

| 5,896,166 A | 4/1999 | D'Alfonso et al. |
| 2004/0147281 A1* | 7/2004 | Holcombe et al. .......... 455/550.1 |

(Continued)

FOREIGN PATENT DOCUMENTS

| EP | 1 894 515 A1 | 3/2008 |
| EP | 2 022 388 A1 | 2/2009 |

(Continued)

OTHER PUBLICATIONS

Extended Supplementary European Search Report dated Jan. 24, 2014 from related European Application No. 12 80 7253.5.

*Primary Examiner* — Frederick Bailey
(74) *Attorney, Agent, or Firm* — Scully, Scott, Murphy & Presser, PC

(57) ABSTRACT

An endoscope system has an image pickup section and a processor. The image pickup section has a control register section which controls a sensor section, a nonvolatile memory which stores first setup data, a control signal interface section which sets the first setup data in the control register section, and an initialization check register which senses an abnormality in the control register section. When an abnormality is sensed, the control signal interface section reads out the setup data from the nonvolatile memory and performs control so as to reset the setup data in the control register section. The control signal interface section further has a memory which stores reset occurrence information upon occurrence of reset. The processor includes a control section which reads out the reset occurrence information from the memory, and, when reset is detected, transmits second setup information held by the processor to the image pickup section.

4 Claims, 8 Drawing Sheets

(51) Int. Cl.
*H04N 3/14* (2006.01)
*A61B 1/00* (2006.01)
*A61B 1/045* (2006.01)
*A61B 1/05* (2006.01)
*H04N 5/357* (2011.01)
*H04N 5/225* (2006.01)

(52) U.S. Cl.
CPC ......... *A61B1/00002* (2013.01); *A61B 1/00006* (2013.01); *A61B 1/00011* (2013.01); *A61B 1/00018* (2013.01)
USPC .............................. 348/65; 600/109; 348/294

(56) References Cited

U.S. PATENT DOCUMENTS

2009/0247824 A1* 10/2009 Kawasaki et al. ............. 600/109
2010/0328512 A1* 12/2010 Davidovici ................... 348/302
2011/0317049 A1* 12/2011 Kurane et al. ................. 348/294

FOREIGN PATENT DOCUMENTS

| JP | 2001-077955 | 3/2001 |
| JP | 2005-342147 | 12/2005 |
| JP | 2010-004146 | 1/2010 |

* cited by examiner

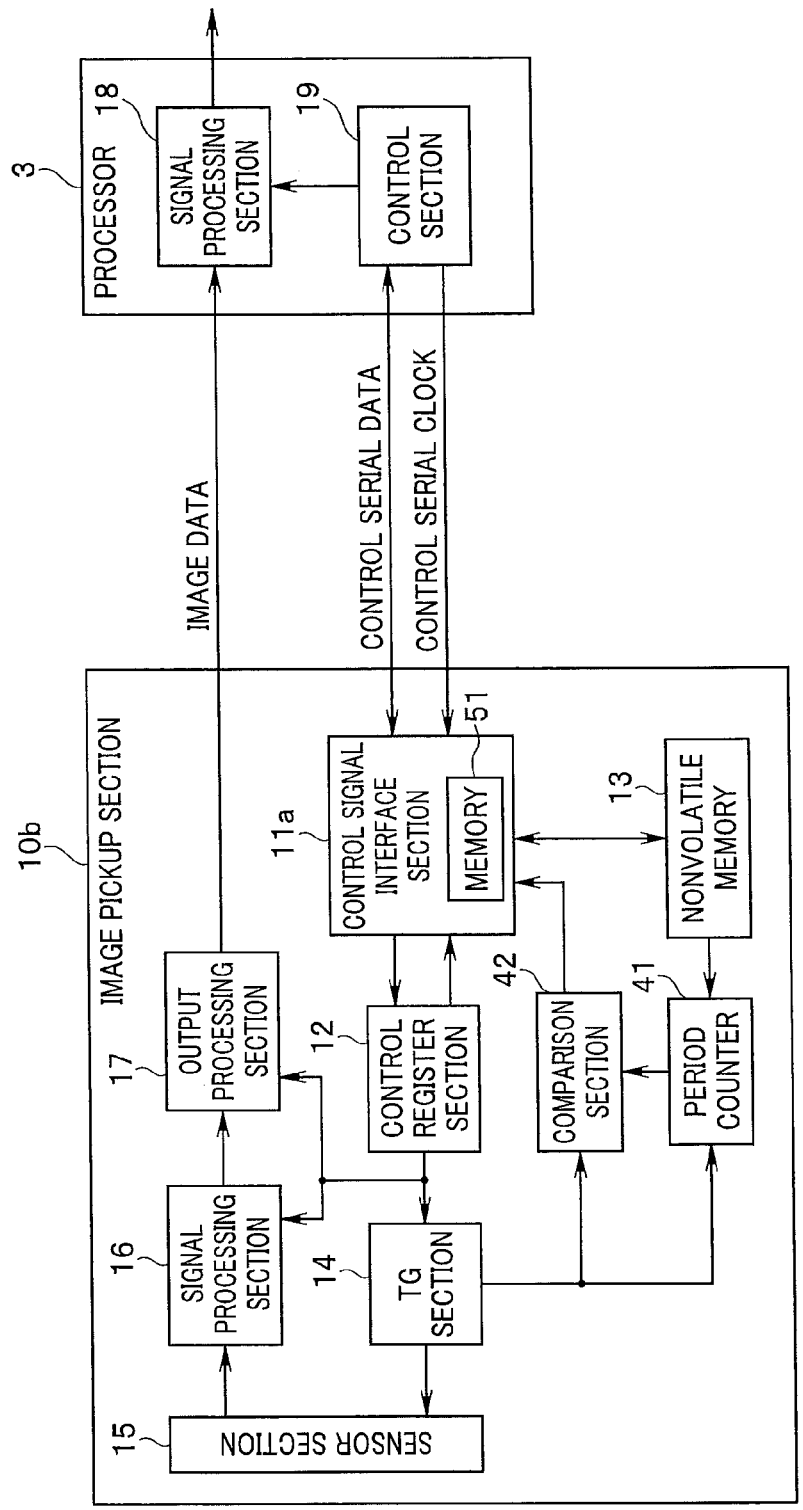

ENDOSCOPE SYSTEM

CROSS REFERENCE TO RELATED APPLICATION

This application is a continuation application of PCT/JP2012/066899 filed on Jul. 2, 2012 and claims benefit of Japanese Application No. 2011-149463 filed in Japan on Jul. 5, 2011, the entire contents of which are incorporated herein by this reference.

BACKGROUND OF THE INVENTION

1. Field of the Invention

The present invention relates to an endoscope system and, more particularly, to an endoscope system which senses an abnormality and sets setup data again.

2. Description of the Related Art

An endoscope, a digital camera, and the like have been well known as image pickup apparatuses provided with, e.g., a CCD sensor or a CMOS sensor. For example, Japanese Patent Application Laid-Open Publication No. 2010-4146 discloses a camera system provided with a CMOS sensor as such an image pickup apparatus.

The camera system has an interface section which holds shutter setup data and the like from an outside and a pixel drive portion which produces a drive pulse for driving a pixel section to perform shutter operation and readout in response to the setup data.

In an endoscope including a CMOS sensor, the CMOS sensor is arranged at a distal end portion of an insertion section. Setup data for producing a drive pulse is inputted from a processor connected to a cable having a cable length of, e.g., several tens of cm to several m to the endoscope. The setup data is held in a register which is provided in the CMOS sensor arranged at the distal end portion of the insertion section and is accessible from an outside.

SUMMARY OF THE INVENTION

An endoscope system according to one aspect of the present invention is an endoscope system including an image pickup apparatus including an image pickup device which picks up an image of an object and a processor connected to the image pickup apparatus. The image pickup apparatus includes an image pickup device control section which controls the image pickup device, a storage section which stores first image pickup device control information to be set in the image pickup device control section, an image pickup device control information setting section which sets the first image pickup device control information stored in the storage section in the image pickup device control section, an abnormality sensing section which senses an abnormality in the image pickup device control section, an image pickup device control information resetting section which reads out the image pickup device control information from the storage section and controls the image pickup device control information setting section to reset the image pickup device control information in the image pickup device control section when an abnormality is sensed by the abnormality sensing section, a reset occurrence information storage section which stores reset occurrence information upon occurrence of the reset by the image pickup device control information resetting section, and a first communication section which transmits and receives information to and from the processor, and the processor includes a second communication section which transmits and receives information to and from the image pickup apparatus and an image pickup device control information retransmission section which reads out the reset occurrence information from the reset occurrence information storage section through the second communication section and the first communication section and, when reset is detected, transmits second image pickup device control information held by the processor to the image pickup apparatus through the second communication section and the first communication section.

BRIEF DESCRIPTION OF THE DRAWINGS

FIG. 8 is a diagram showing a configuration of an image pickup section according to a third embodiment.

DETAILED DESCRIPTION OF THE PREFERRED EMBODIMENTS

Embodiments of the present invention will be described below in detail with reference to the drawings.

(First Embodiment)

First, a configuration of an endoscope system including an image pickup apparatus according to a first embodiment of the present invention will be described with reference to FIG. 1.

Figure 1:
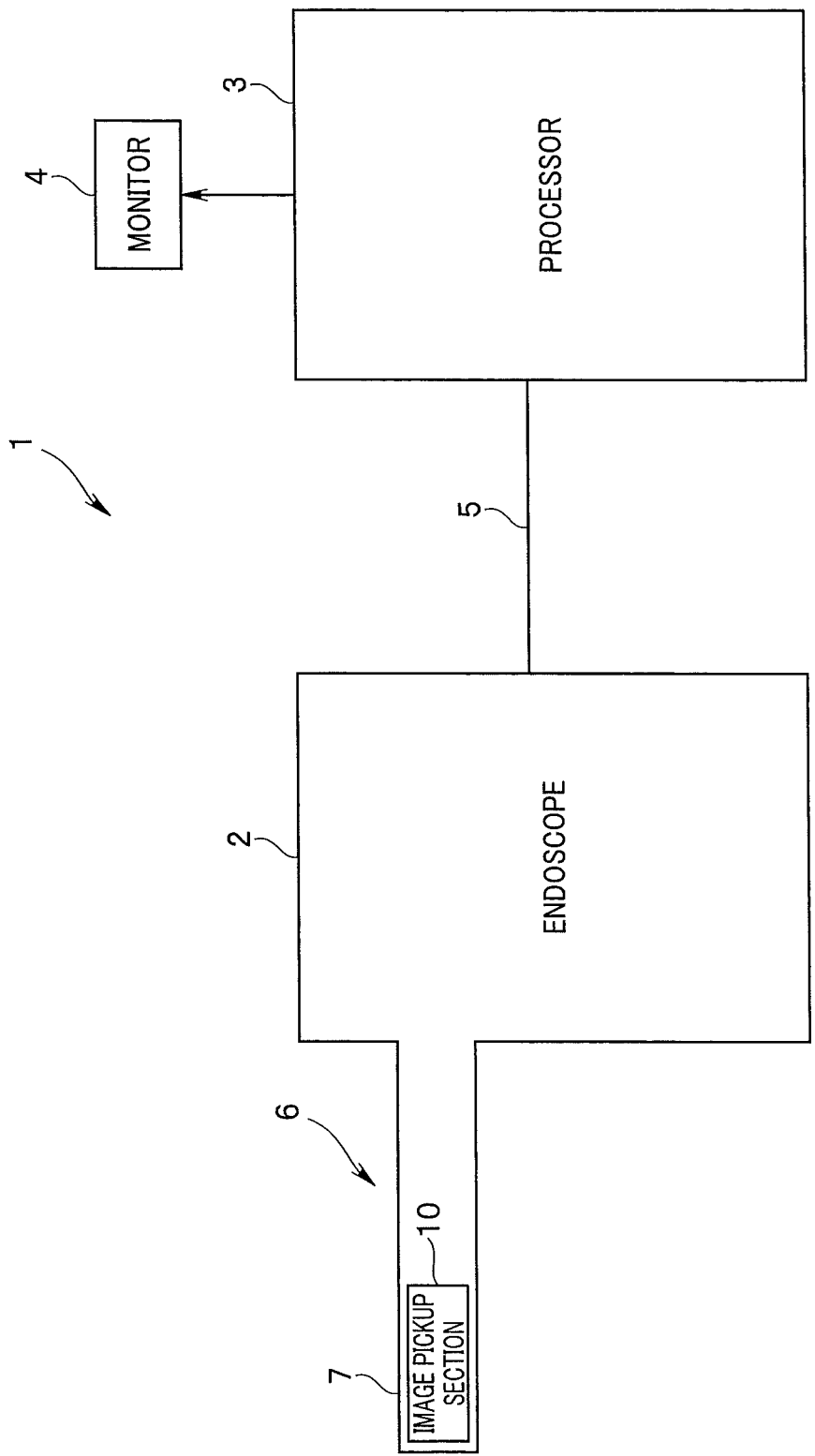
FIG. 1 is a diagram showing a configuration of an endoscope system including an image pickup apparatus according to a first embodiment of the present invention.

FIG. 1 is a diagram showing the configuration of the endoscope system including the image pickup apparatus according to the first embodiment of the present invention.

As shown in FIG. 1, an endoscope system 1 has an endoscope 2 which picks up an image of an object inside a living body and outputs an image pickup signal, a processor 3 which converts the image pickup signal outputted from the endoscope 2 to a video signal and outputs the video signal, a monitor 4 which displays an image corresponding to the video signal outputted from the processor 3, and a cable 5 which connects the endoscope 2 and processor 3. The cable 5 has a cable length of, e.g., several tens of cm to several m.

The endoscope 2 includes an elongated flexible insertion section 6 which can be inserted into a living body. A distal end portion 7 is provided at a distal end of the insertion section 6. An image pickup section 10 which picks up an image of an object and is composed of, e.g., a CMOS sensor is provided at the distal end portion 7.

The image pickup section 10 as an image pickup apparatus according to the present embodiment performs pickup of an image of an object according to setup data on a drive pulse, an image pickup period, a shutter (exposure time period), and the like and readout of an image pickup signal obtained through the image pickup and outputs the image pickup signal to the processor 3 through the cable 5. A detailed configuration of the image pickup section 10 provided at the distal end portion 7 will be described with reference to FIGS. 2 and 3.

Figure 2:
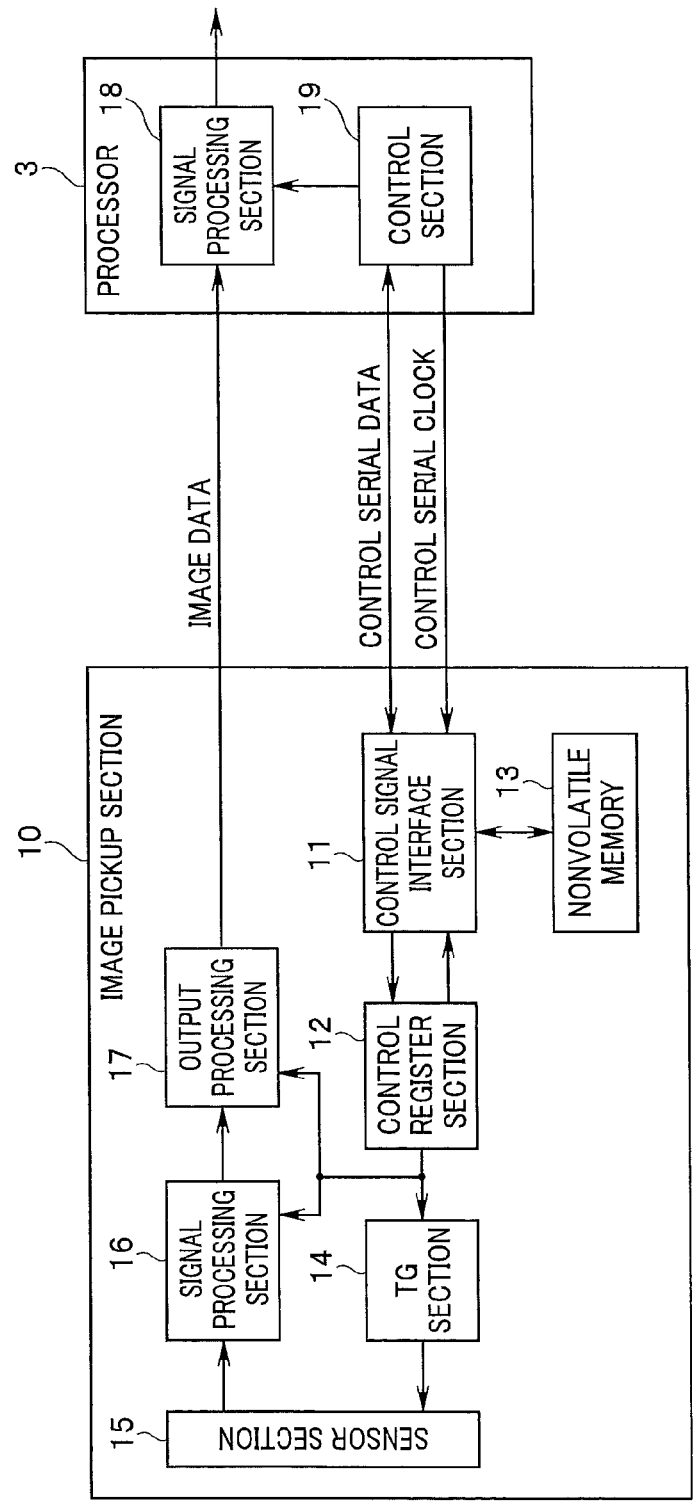
FIG. 2 is a diagram showing a configuration of an image pickup section according to the first embodiment.
Figure 3:
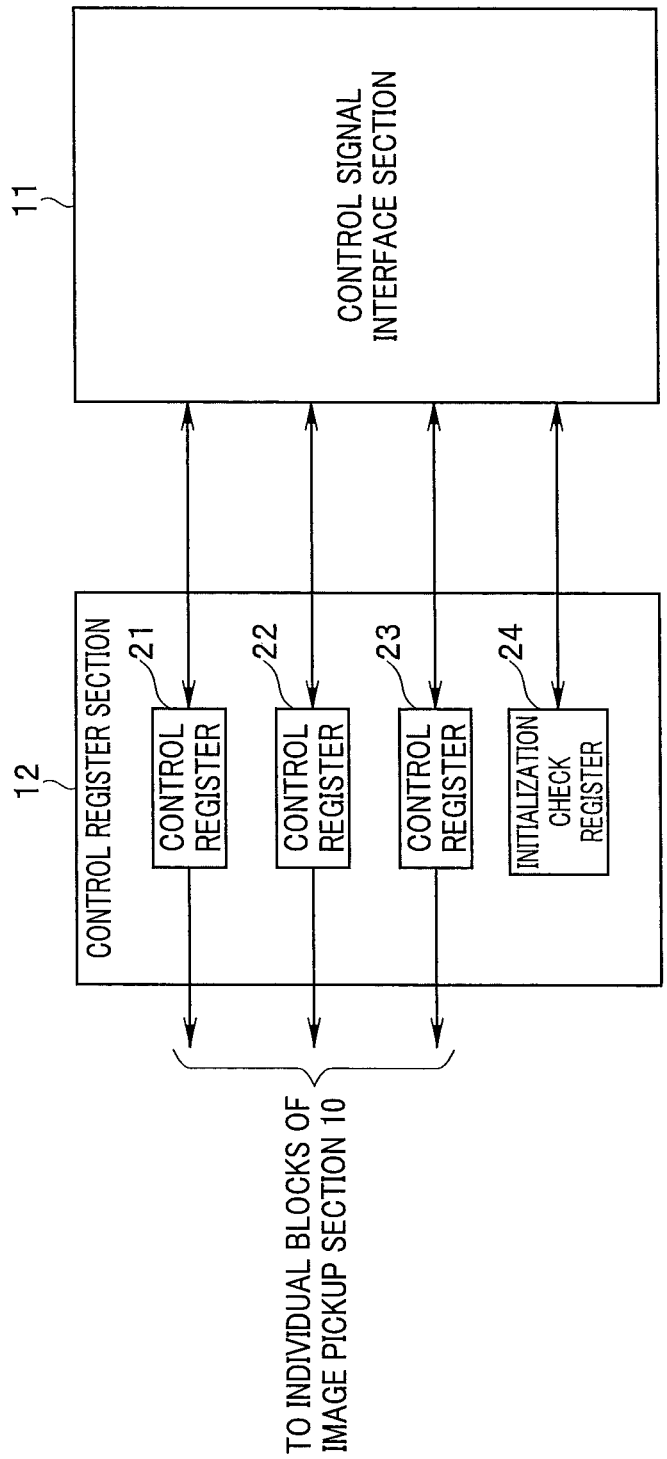
FIG. 3 is a diagram for describing a detailed configuration of a control register section.

FIG. 2 is a diagram showing a configuration of the image pickup section according to the first embodiment, and FIG. 3 is a diagram for describing a detailed configuration of a control register section.

The image pickup section 10 has a control signal interface section 11, a control register section 12, a nonvolatile memory 13, a timing generator (hereinafter referred to as a TG) section 14, a sensor section 15, a signal processing section 16, and an output processing section 17. The processor 3 has a signal processing section 18 and a control section 19.

Setup data (image pickup device control information) on a drive pulse, an image pickup period, and a shutter (exposure time period) which is set on power-up is stored in the nonvolatile memory 13 as a storage section. Use of a nonvolatile memory allows a reduction in likelihood of loss of setup data. Note that a nonvolatile memory is different in semiconductor process step from the TG section 14, signal processing section 16, and the like and that the components are implemented as two chips. The configuration suffers from the problems of costliness and difficulty of size reduction. Note that a volatile memory higher in source voltage than the control register section 12 or the like may be used instead of the nonvolatile memory 13. Use of such a volatile memory high in source voltage can increase noise immunity. Since a denominator of the ratio of noise amplitude to power source amplitude is large, the volatile memory can reduce influence of noise, though to a lesser extent than a nonvolatile memory. A volatile memory can be fabricated in a same semiconductor process step for the TG section 14, signal processing section 16, and the like, and the components can be fabricated as one chip. The configuration facilitates cost reduction and size reduction.

The control signal interface section 11 as an image pickup device control information setting section reads out the setup data stored in the nonvolatile memory 13 on power-up and outputs the read-out setup data to the control register section 12. Desired setup data set by a user is supplied as control serial data from the control section 19 of the processor 3 to the control signal interface section 11. The control signal interface section 11 takes in the desired setup data supplied from the control section 19 on the basis of a control serial clock and outputs the desired setup data to the control register section 12.

As shown in FIG. 3, the control register section 12 as an image pickup device control section has a plurality of (three in the present embodiment) control registers 21, 22, and 23 and an initialization check register 24. Note that although the control register section 12 has the three control registers 21 to 23, the number of control registers is not limited to three.

The control registers 21 to 23 hold pieces of setup data outputted from the control signal interface section 11. The control registers 21 to 23 supply the held pieces of setup data to individual sections (the TG section 14, signal processing section 16, and output processing section 17 in the present embodiment) of the image pickup section 10.

The initialization check register 24 constitutes an abnormality detection section which detects an abnormality that pieces of setup data held in the control registers 21 to 23 are rewritten due to noise of a radio knife or the like. The initialization check register 24 outputs a control register abnormality detection signal indicating whether an abnormality that pieces of setup data in the control registers 21 to 23 are rewritten has occurred to the control signal interface section 11.

When a control register abnormality detection signal indicating that the control registers 21 to 23 have an abnormality is inputted from the initialization check register 24, the control signal interface section 11 as an image pickup device control information resetting section reads out the setup data stored in the nonvolatile memory 13 and outputs the setup data to the control register section 12 again to set the setup data.

The TG section 14 produces a drive pulse for driving the sensor section 15 on the basis of a piece of setup data from the control register section 12 and outputs the drive pulse to the sensor section 15.

The sensor section 15 as an image pickup device photoelectrically converts an optical image of an object on the basis of the drive pulse from the TG section 14 and produces an image pickup signal. The sensor section 15 outputs the produced image pickup signal to the signal processing section 16.

The signal processing section 16 subjects the image pickup signal outputted from the sensor section 15 to predetermined signal processing and outputs the image pickup signal to the output processing section 17.

The output processing section 17 performs a process of outputting the image pickup signal subjected to the predetermined signal processing in the signal processing section 16 to the signal processing section 18 of the processor 3 using a predetermined transfer system.

The signal processing section 18 of the processor 3 performs a signal process of converting the image pickup signal from the output processing section to a video signal and outputs the video signal to the monitor 4.

Operation when an abnormality has occurred in setup data in the control register section 12 will be described with reference to FIG. 3.

The initialization check register 24 holds 0 in an initial state in which pieces of setup data are not written from the control signal interface section 11. When the control registers 21 to 23 hold pieces of setup data, 0 is rewritten to 1 under control of the control signal interface section 11, and the initialization check register 24 holds the value. The initialization check register 24 supplies the held value as a control register abnormality detection signal to the control signal interface section 11. When an abnormality occurs in the pieces of setup data due to noise of a radio knife or the like, and the value is rewritten from 1 to 0 in the initialization check register 24, it is determined that an abnormality has occurred. Note that although the initialization check register 24 holds 1-bit data, the initialization check register 24 may hold multi-bit data. For example, the initialization check register 24 is configured to hold 8-bit data, and bits are all rewritten to 1 when pieces of setup data are set. If four or more bits of data are changed to 0 in the initialization check register 24, it is determined that an abnormality has occurred. The redundancy of data in the initialization check register 24 allows avoidance of erroneous determination caused by noise produced at the time of, e.g., data readout.

When a control register abnormality detection signal supplied from the initialization check register 24 is changed from 1 to 0, the control signal interface section 11 determines that an abnormality has occurred in the pieces of setup data held in the control registers 21 to 23, reads out the setup data from the nonvolatile memory 13, and outputs the setup data to the control register section 12. With the process, the control registers 21 to 23 hold pieces of setup data again. As a result, the image pickup section 10 can perform image pickup corresponding to the set pieces of setup data.

A different configuration of the control register section 12 will be described.

Figure 4:
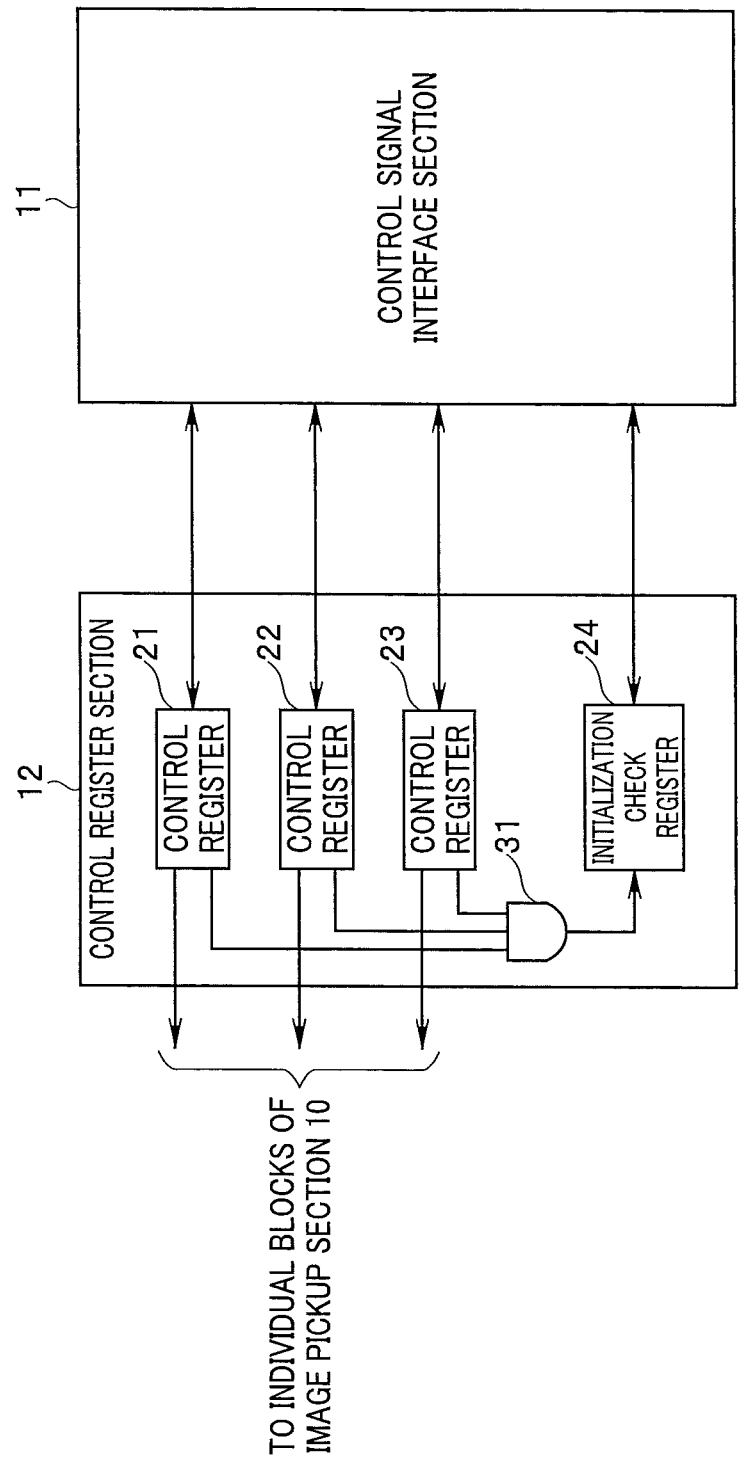
FIG. 4 is a diagram for describing another configuration of the control register section.

FIG. 4 is a diagram for describing another configuration of the control register section.

In the example in FIG. 3, when pieces of setup data are set by the control signal interface section 11, the value in the initialization check register 24 is rewritten from 0 to 1 under control of the control signal interface section 11. In contrast, in the example in FIG. 4, when pieces of setup data are set by the control signal interface section 11, the initialization check register 24 is automatically rewritten from 0 to 1.

The control register section 12 is constructed by adding an AND circuit 31 to the configuration in FIG. 3. Initial state signals A1 to A3 are inputted from the control registers 21 to 23 to the AND circuit 31. In the initial state in which respective pieces of setup data are not written from the control signal interface section 11, the control registers 21 to 23 output 0 as the initial state signals A1 to A3 to the AND circuit 31. In a state in which pieces of setup data are written from the control signal interface section 11, the control registers 21 to 23 output 1 as the initial state signals A1 to A3 to the AND circuit 31.

When the initial state signals A1 to A3 are all 1, the AND circuit 31 outputs 1 to the initialization check register 24. When pieces of setup data are written from the processor 3 to the control registers 21 to 23, the initialization check register 24 is rewritten from 0 indicating the initial state to 1 indicating completion of setting in the above-described manner.

Configurations of the control registers 21 to 23 that output the initial state signals A1 to A3 will be described.

Figure 5:
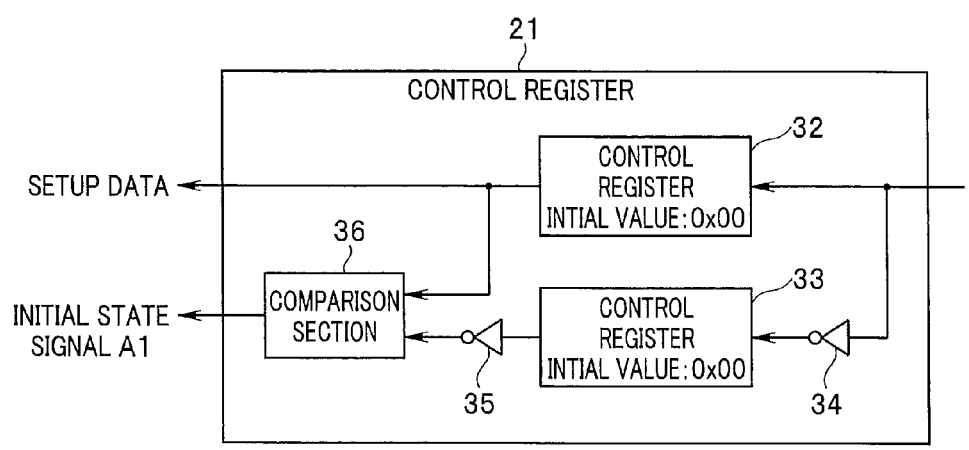
FIG. 5 is a diagram for describing a configuration of a control register.

FIG. 5 is a diagram for describing a configuration of a control register. Note that the control registers 21 to 23 have a same configuration and that a configuration of the control register 21 will be described on behalf of the control registers 21 to 23.

The control register 21 has control registers 32 and 33, inverter circuits 34 and 35, and a comparison section 36.

The control registers 32 and 33 hold 00 as initial values. The initial value of the control register 32 is supplied to the comparison section 36. The initial value of the control register 33 is inverted by the inverter circuit 35 and is supplied to the comparison section 36. That is, in the initial state in which pieces of setup data are not written from the control signal interface section 11, 00 from the control register 32 and 11 from the inverter circuit 35 are inputted to the comparison section 36. As described above, in the initial state, different values are inputted from the control register 32 and inverter circuit 35 to the comparison section 36.

When a piece of setup data is supplied from the control signal interface section 11 to the control register 21, the control register 32 holds the piece of setup data. The piece of setup data held in the control register 32 is supplied to individual sections of the image pickup section 10 and is also supplied to the comparison section 36. For example, the piece of setup data is 11, 11 is inputted from the control register 32 to the comparison section 36.

The piece of setup data from the control signal interface section 11 is inverted by the inverter circuit 34 and is held by the control register 33. The piece of setup data held in the control register 33 is inverted by the inverter circuit 35 and is outputted to the comparison section 36. That is, if the piece of setup data is 11, the piece of setup data is inverted by the inverter circuit 34, and 00 is held by the control register 33. After that, 00 is inverted by the inverter circuit 35, and 11 is supplied to the comparison section 36. As described above, when a piece of setup data is written from the control signal interface section 11, same values are inputted from the control register 32 and inverter circuit 35 to the comparison section 36.

The comparison section 36 compares a value from the inverter circuit 35 with a value from the control register 32. If the values do not coincide with each other, the comparison section 36 outputs 0 as the initial state signal A1. On the other hand, if the values coincide with each other, the comparison section 36 outputs 1 as the initial state signal A1. That is, the comparison section 36 outputs 0 to the AND circuit 31 in the initial state and outputs 1 to the AND circuit 31 when a piece of setup data is written.

The control registers 22 and 23 have a same configuration. Each of the control registers 22 and 23 outputs 0 to the AND circuit 31 in the initial state and outputs 1 to the AND circuit 31 when a corresponding piece of setup data is written. When respective pieces of setup data are written to all the control registers 21 to 23, the initial state signals A1 to A3 are all 1, and 1 is outputted from the AND circuit 31 to the initialization check register 24. In the above-described manner, the initialization check register 24 is rewritten from 0 indicating the initial state to 1 indicating completion of setting.

Other operations are same as in FIG. 3. That is, when an abnormality occurs in pieces of setup data due to noise of a radio knife or the like, and the value is rewritten from 1 to 0 in the initialization check register 24, it is determined that an abnormality has occurred. When a control register abnormality detection signal supplied from the initialization check register 24 is changed from 1 to 0, the control signal interface section 11 determines that an abnormality has occurred in the pieces of setup data held in the control registers 21 to 23, reads out the setup data from the nonvolatile memory 13, and outputs the setup data to the control register section 12. With the process, the control registers 21 to 23 of the control register section 12 hold pieces of setup data again. As a result, the image pickup section 10 can perform image pickup corresponding to the set pieces of setup data.

As has been described above, when the image pickup section 10 as the image pickup apparatus according to the present embodiment detects that an abnormality has occurred in pieces of setup data set in the control register section 12 due to noise or the like, the image pickup section 10 reads the setup data stored in the nonvolatile memory 13 and sets the setup data in the control register section 12 again. As a result, the image pickup section 10 can set the setup data stored in the nonvolatile memory 13 in the control register section 12 again and perform image pickup corresponding to the setup data set again even if poor image output occurs due to influence of noise.

Therefore, the image pickup apparatus according to the present embodiment can ensure normal image output even under influence of noise.

(Second Embodiment)

A second embodiment will be described.

Figure 6:
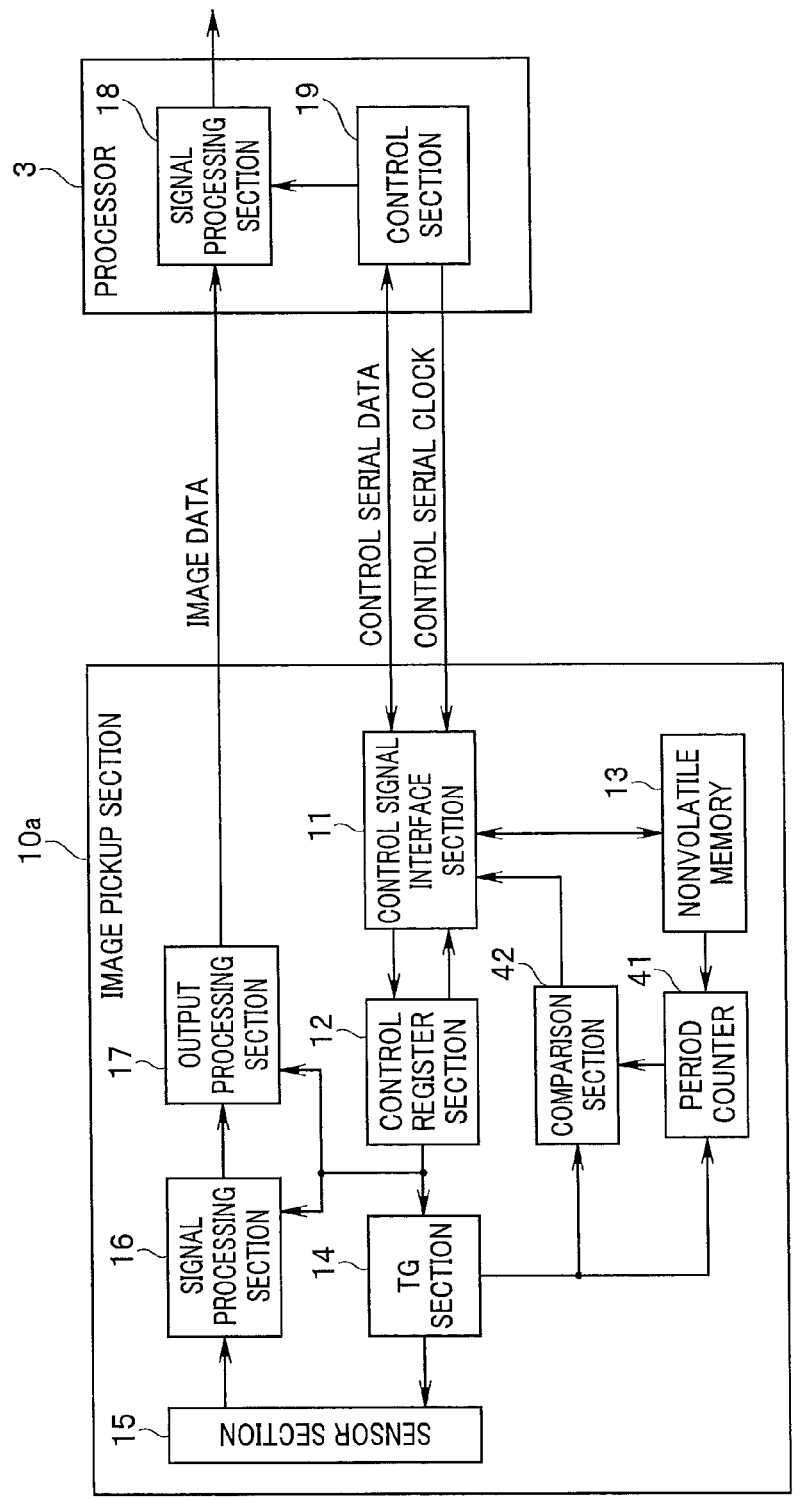
FIG. 6 is a diagram showing a configuration of an image pickup section according to a second embodiment.

FIG. 6 is a diagram showing a configuration of an image pickup section according to the second embodiment. Note that same components in FIG. 6 as components in FIG. 2 are denoted by same reference numerals and a description of the components will be omitted.

As shown in FIG. 6, an image pickup section 10a is constructed by adding a period counter 41 and a comparison section 42 to the image pickup section 10 in FIG. 2.

A pulse from a TG section 14 is supplied to the period counter 41 and comparison section 42. Pulse information stored in a nonvolatile memory 13 is supplied to the period counter 41.

The period counter 41 with a pulse corresponding to the pulse information stored in the nonvolatile memory 13 resets itself with a pulse from the TG section 14 and produces pulses with a same period as a period of pulses from the TG section 14. The period counter 41 outputs pulses generated with the same period as the period of pulses from the TG section 14 to the comparison section 42. Note that a plurality of period counters 41 may be provided so as to correspond to a plurality of pulses. Examples of a pulse from the TG section 14 include a pulse with a frame period and a pulse with a horizontal line period. A plurality of period counters 41 are provided so as to correspond in number to pulses.

The comparison section 42 compares the period of pulses from the TG section 14 and the period of pulses from the period counter 41. If pulses occur simultaneously, the comparison section 42 determines that there is no abnormality in pieces of setup data in control registers 21 to 23. If a pulse from the TG section 14 occurs later than a pulse from the period counter 41 (the period of pulses from the TG section 14 is longer) or a pulse from the TG section 14 occurs earlier than a pulse from the period counter 41 (the period of pulses from the TG section 14 is shorter), the comparison section 42 determines that there is an abnormality in the pieces of setup data in the control registers 21 to 23. The comparison section 42 outputs an abnormality determination signal to a control signal interface section 11 if the comparison section 42 determines that there is an abnormality in the pieces of setup data in the control registers 21 to 23.

When the abnormality determination signal is inputted from the comparison section 42, the control signal interface section 11 reads out setup data stored in the nonvolatile memory 13, sets pieces of setup data in the control registers 21 to 23 of a control register section 12 again, and maintains operation of the image pickup section 10a.

Operation of the image pickup section 10a with the above-described configuration will be described.

FIG. 7 are charts for describing examples of pulses generated at the TG section and period counter.

Figure 7A:
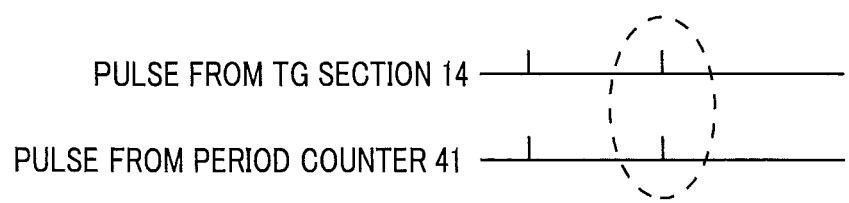
FIG. 7A is a chart for describing an example in which a pulse from a TG section 14 and a pulse from a period counter 41 occur simultaneously.
Figure 7B:
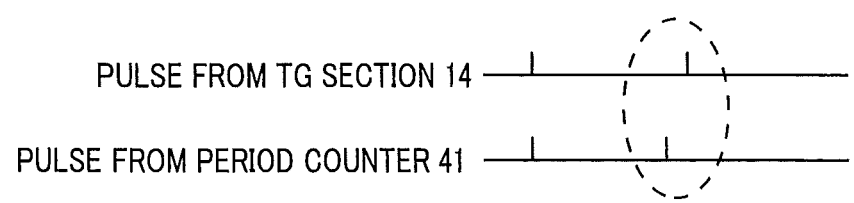
FIG. 7B is a chart for describing an example in which a pulse from the TG section 14 occurs later than a pulse from the period counter 41.
Figure 7C:
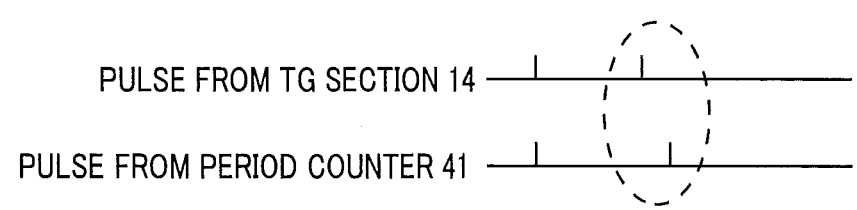
FIG. 7C is a chart for describing an example in which a pulse from the TG section 14 occurs earlier than a pulse from the period counter 41.

FIG. 7A is an example in which a pulse from the TG section 14 and a pulse from the period counter 41 occur simultaneously. FIG. 7B is an example in which a pulse from the TG section 14 occurs later than a pulse from the period counter 41. FIG. 7C is an example in which a pulse from the TG section 14 occurs earlier than a pulse from the period counter 41.

If a pulse from the TG section 14 and a pulse from the period counter 41 occur simultaneously, as shown in FIG. 7A, the comparison section 42 determines that there is no abnormality in the pieces of setup data in the control registers 21 to 23. If a pulse from the TG section 14 occurs later than a pulse from the period counter 41, i.e., the period of pulses from the TG section 14 is longer than the period of pulses from the period counter 41, as shown in FIG. 7B, the comparison section 42 determines that there is an abnormality in the pieces of setup data in the control registers 21 to 23. Similarly, if a pulse from the TG section 14 occurs earlier than a pulse from the period counter 41, i.e., the period of pulses from the TG section 14 is shorter than the period of pulses from the period counter 41, as shown in FIG. 7C, the comparison section 42 determines that there is an abnormality in the pieces of setup data in the control registers 21 to 23.

If the comparison section 42 determines that there is an abnormality in the pieces of setup data in the control register section 12, an abnormality determination signal is outputted from the comparison section 42 to the control signal interface section 11. When the abnormality determination signal is inputted from the comparison section 42 to the control signal interface section 11, the setup data stored in the nonvolatile memory 13 is read out and is outputted to the control register section 12. With the process, pieces of setup data are set in the control register section 12 again, and operation of the image pickup section 10a is maintained.

As has been described above, the image pickup section 10a according to the present embodiment can ensure normal image output even under influence of noise, like the image pickup section 10 according to the first embodiment.

(Third Embodiment)

A third embodiment will be described.

FIG. 8 is a diagram showing a configuration of an image pickup section according to the third embodiment. Note that same components in FIG. 8 as components in FIG. 6 are denoted by same reference numerals and a description of the components will be omitted.

As shown in FIG. 8, an image pickup section 10b is constructed by using a control signal interface section 11a instead of the control signal interface section 11 in FIG. 6.

The control signal interface section 11a has a memory 51. When setup data is set in a control register section 12 again by the control signal interface section 11a, reset occurrence information is stored in the memory 51 as a reset occurrence information storage section. The reset occurrence information is read out to a control section 19 of a processor 3 through the control signal interface section 11a constituting a first communication section.

The control section 19 of the processor 3 reads out the reset occurrence information stored in the memory 51. If the control section 19 determines that an abnormality has occurred in the image pickup section 10b and setup data is reset, the control section 19 transmits setup data transferred from the processor 3 before the occurrence of the abnormality, setup data arbitrarily set by a user using the processor 3 in the present embodiment, to the control signal interface section 11a of the image pickup section 10b. As described above, the control section 19 constitutes a second communication section and an image pickup device control information retransmission section which transmits the setup data arbitrarily set by the user to the control signal interface section 11a of the image pickup section 10b if reset is performed.

As described above, the image pickup section 10b reads out setup data which is set on power-up from a nonvolatile memory 13 and sets the setup data in the control register section 12 again when an abnormality occurs in the control register section 12. With the configuration, the image pickup section 10b can return quickly from a poor image output state to a normal image pickup state. The image pickup section 10b stores the reset occurrence information indicating that the setup data is set again in the memory 51. When the control section 19 of the processor 3 reads out the reset occurrence information and senses that reset has been performed in the image pickup section 10b, the control section 19 outputs the setup data arbitrarily set by the user through the processor 3 to the control signal interface section 11a and sets the setup data in the control register section 12.

As has been described above, the image pickup section 10b according to the present embodiment can ensure normal image output even under influence of noise and can perform image pickup corresponding to setup data arbitrarily set by a user before reception of influence of noise.

Note that although the image pickup section described in each of the above-described embodiments is provided at the distal end portion 7 of the insertion section 6, the image pickup section may be provided at, for example, a camera head of a rigid endoscope or the like.

The present invention is not limited to the above-described embodiments, and various changes and modifications may be made without departing from scope of the present invention.

What is claimed is:

1. An endoscope system comprising:
   an image pickup apparatus including an image pickup device which picks up an image of an object and a processor connected to the image pickup apparatus,
   wherein the image pickup apparatus includes
   an image pickup device control section which controls the image pickup device,
   a storage section which stores first image pickup device control information to be set in the image pickup device control section,
   an image pickup device control information setting section which sets the first image pickup device control information stored in the storage section in the image pickup device control section,
   a pulse generating section which generates a first pulse for driving the image pickup device based on the first image pickup device control information set in the image pickup device control section,
   a period counter which resets a second pulse corresponding to the first image pickup device control information stored in the storage section, by the first pulse generated by the pulse generating section, to produce the second pulse with the same period as the first pulse,
   a comparison section which compares a period of the first pulse and a period of the second pulse, and determines an abnormality in the first image pickup device control information set in the image pickup device control section by the image pickup device control information setting section and outputs an abnormality determination signal if the period of the first pulse is longer or shorter than the period of the second pulse,
   an image pickup device control information resetting section which reads out the image pickup device control information from the storage section and controls the image pickup device control information setting section to reset the image pickup device control information in the image pickup device control section when the abnormality determination signal is inputted from the comparison section,
   a reset occurrence information storage section which stores reset occurrence information upon occurrence of the reset by the image pickup device control information resetting section, and
   a first communication section which transmits and receives information to and from the processor, and
   the processor includes
   a second communication section which transmits and receives information to and from the image pickup apparatus; and
   an image pickup device control information retransmission section which reads out the reset occurrence information from the reset occurrence information storage section through the second communication section and the first communication section and, when reset is detected, transmits second image pickup device control information held by the processor to the image pickup apparatus through the second communication section and the first communication section.

2. The endoscope system according to claim 1, wherein the storage section is a nonvolatile memory.

3. The endoscope system according to claim 1, wherein the storage section operates on a power source having a voltage higher than a voltage of a power source of the image pickup device control section.

4. The endoscope system according to claim 1, wherein the image pickup apparatus and the processor are connected through a cable.

\* \* \* \* \*